(12) United States Patent
Thedieck et al.

(10) Patent No.: US 10,041,933 B2
(45) Date of Patent: Aug. 7, 2018

(54) MODULATORS OF THE INTERACTION OF ASTRIN AND RAPTOR, AND USES THEREOF IN CANCER THERAPY

(71) Applicant: ALBERT-LUDWIGS-UNIVERSITÄT FREIBURG, Freiburg (DE)

(72) Inventors: Kathrin Thedieck, KR Haren (NL); Birgit Holzwarth, Ehrenkirchen (DE); Ralf Baumeister, Freiburg (DE)

(73) Assignee: ALBERT-LUDWIGS-UNIVERSITÄT FREIBURG, Freiburg (DE)

( * ) Notice: Subject to any disclaimer, the term of this patent is extended or adjusted under 35 U.S.C. 154(b) by 139 days.

(21) Appl. No.: 14/758,461

(22) PCT Filed: Jan. 13, 2014

(86) PCT No.: PCT/EP2014/050460
§ 371 (c)(1),
(2) Date: Jun. 29, 2015

(87) PCT Pub. No.: WO2014/108532
PCT Pub. Date: Jul. 17, 2014

(65) Prior Publication Data
US 2015/0355166 A1 Dec. 10, 2015

(30) Foreign Application Priority Data
Jan. 11, 2013 (EP) .................................. 13151022

(51) Int. Cl.
*C12N 15/11* (2006.01)
*G01N 33/50* (2006.01)

(52) U.S. Cl.
CPC ...... *G01N 33/5011* (2013.01); *C12N 2310/14* (2013.01)

(58) Field of Classification Search
USPC .............. 435/6.1; 536/23.1, 24.5; 424/134.1; 514/44
See application file for complete search history.

(56) References Cited

PUBLICATIONS

Thedieck et al. 2013. Cell, vol. 154:859-874.*
Cheng, T.-S. et al., "Glycogen Synthase Kinase 3 Interacts with and Phosphorylates the Spindle-associated Protein Astrin," *Journal of Biological Chemistry*, 2007, 283(4):2454-2464.
Du, J. et al., "Astrin regulates Aurora-A localization," *Biochemical and Biophysical Research Communications, Academic Press Inc.*, 2008, 370(2):213-219.
Yang, Y. C. et al: "Silencing of astrin induces the p53-dependent apoptosis by suppression of HPV18 E6 expression and sensitizes cells to paclitaxel treatment in HeLa cells," *Biochemical and Biophysical Research Communications, Academic Press Inc.*, 2006, 343(2):428-434.

* cited by examiner

*Primary Examiner* — Terra C Gibbs
(74) *Attorney, Agent, or Firm* — Saliwanchik, Lloyd & Eisenschenk

(57) ABSTRACT

The present invention relates to modulators of the interaction of astrin and raptor, and their uses in the treatment of mTOR related diseases, such as cancer.

6 Claims, 6 Drawing Sheets

MODULATORS OF THE INTERACTION OF ASTRIN AND RAPTOR, AND USES THEREOF IN CANCER THERAPY

CROSS REFERENCE TO RELATED APPLICATIONS

This application is a National Stage Application of International Application Number PCT/EP2014/050460, filed Jan. 13, 2014; which claims priority to European Application No. 13151022.4, filed Jan. 11, 2013; all of which are incorporated herein by reference in their entirety.

The Sequence Listing for this application is labeled "SeqList-29Jun15.txt", which was created on Jun. 29, 2015, and is 11 KB. The entire content is incorporated herein by reference in its entirety.

The present invention relates to modulators of the interaction of astrin and raptor, and their uses in the treatment of mTOR related diseases, such as cancer.

DESCRIPTION

The discovery of rapamycin from a soil sample on the Easter Island in the mid 60's marked the beginning of an exciting field of research in cell biology and medicine. While it was first used as an antifungal and as an immunosuppressive drug, more recent studies confirmed rapamycin's antiproliferative properties over a variety of solid tumors. Research aimed at identifying its mechanism of action uncovered mTOR (mammalian target of rapamycin), a protein kinase that regulates mRNA translation and protein synthesis, an essential step in cell division and proliferation. mTOR is part of the PI3K/AKT/mTOR pathway, an intracellular signaling pathway important in apoptosis and hence cancer e.g. breast cancer and non-small-cell lung cancer. PI3K activation activates AKT which activates mTOR. In many cancers this pathway is overactive reducing apoptosis and allowing proliferation. Thus some experimental cancer drugs aim to inhibit the signaling sequence at some point, and several anti-cancer therapies based on mTOR inhibition are pursued.

As one example, Zagouri et al. (in: Zagouri F, Sergentanis T N, Chrysikos D, Filipits M, Bartsch R. mTOR inhibitors in breast cancer: A systematic review. Gynecol Oncol. 2012 Sep. 8) describe PI3K/AKT/mTOR pathway as a crucial mediator of tumor progression. LoRusso P M. Mammalian target of rapamycin as a rational therapeutic target for breast cancer treatment. Oncology. 2013; 84(1):43-56. Epub 2012 Oct. 30 describes that a number of agents that are target of the mTOR pathway have shown potent antitumorigenic effects in vitro, and several agents have also shown promise in treating patients with breast cancer, such as everolimus and temsirolimus. As the PI3K/Akt pathway is heavily deregulated in breast cancer, the application of mTOR inhibitors in breast cancer patients seems warranted. This is the first systematic review according to PRISMA guidelines to synthesize all available data of mTOR inhibitors in all subcategories of breast cancer. The search strategy retrieved 16 studies evaluating everolimus (1492 patients), seven studies examining temsirolimus (1245 patients), one study evaluating sirolimus (400 patients) and two studies evaluating MKC-1 (60 patients). The Breast Cancer Trials of Oral Everolimus-2 (BOLERO-2) study has marked a turning point in the evaluation of everolimus in the treatment of estrogen receptor positive breast cancer. Given the positive results, everolimus has entered NCCN 2012 guidelines, and its approval of its combination with exemestane by FDA and EMA is imminent. In addition, the promising antitumor activity and long-term disease control further suggest that mTOR inhibition with everolimus may provide an avenue for achieving long-lasting benefit from trastuzumab-based therapy in HER2-positive patients. Regarding temsirolimus, it seems that the agent may play, in the future, a role in the treatment of metastatic breast cancer; importantly, however, there is an unmet need to find its optimal target subpopulation. mTOR inhibitors currently in clinical studies for tumour and metabolic diseases are also described in Inoki et al. (Inoki, K., Kim, J., and Guan, K. L. (2012). AMPK and mTOR in cellular energy homeostasis and drug targets. Annu Rev Pharmacol Toxicol 52, 381-400).

mTOR complex 1 (mTORC1) also comprises the protein raptor (regulatory associated protein of mTOR). mTOR controls cell growth, in part by regulating p70 S6 kinase alpha (p70alpha) and eukaryotic initiation factor 4E binding protein 1 (4EBP1). Raptor is an essential scaffold for the mTOR-catalyzed phosphorylation of 4EBP1 and mediates TOR action in vivo.

Kapoor et al. (in: Kapoor V, Zaharieva M M, Das S N, Berger M R. Erufosine simultaneously induces apoptosis and autophagy by modulating the Akt-mTOR signaling pathway in oral squamous cell carcinoma. Cancer Lett. 2012 Jun. 1; 319(1):39-48. Epub 2011 Dec. 24) describe the investigation of the anticancer activity of erufosine in oral squamous carcinoma cell lines in terms of cell proliferation, colony formation, induction of autophagy/apoptosis, cell cycle and mTOR signaling pathway. Erufosine showed dose-dependent cytotoxicity in all cell lines, it induced autophagy as well as apoptosis, G2 cell cycle arrest and modulation of cyclin Dl expression. Further erufosine downregulated the phosphorylation of major components of mTOR pathway, like p-Akt at Ser473 and Thr308 residues, p-raptor, p-mTOR, p-PRAS40 and its downstream substrates p-p70S6K and p-4EBP1 in a dose-dependent manner. The pretreatment of tumor cells with p-mTOR siRNA increased cytotoxic effects of erufosine comparable to cisplatin but higher than rapamycin.

The protein astrin (also designated spag5) has previously been described as a spindle-associated protein involved in mitotic progression (Thein K H, Kleylein-Sohn J, Nigg E A, Gruneberg U. Astrin is required for the maintenance of sister chromatid cohesion and centrosome integrity. J Cell Biol. 2007 Jul. 30; 178(3):345-54). The dual localization of astrin to both centrosomes and kinetochores indicates that it may be required for spindle formation and chromosome segregation. Astrin comprises 5' TOP mRNA sequences, a feature shared by many mTOR regulated translation factors.

Välk et al (in Välk K, Vooder T, Kolde R, Reintam M A, Petzold C, Vilo J, Metspalu A, Gene expression profiles of non-small cell lung cancer: survival prediction and new biomarkers. Oncology. 2010; 79 (3-4):283-92. Epub 2011 Mar. 16) describe the upregulation of the expression of SPAG5 in non-small cell lung cancer.

Abdel-Fatah T. et al (in A study of Sperm-associated Antigen 5 (SPAG5) in predicting response to Anthracycline (ATC)/Platinum Chemotherapies (CT) in breast (BC) & Ovarian Cancers (OVC) Virchows Arch (2012) 461 (Suppl 1):S1-S332) describe SPAG5 as a novel gene implicated in the survival of BC and OVC cells and its protein expression is an independent predictor for anthracycline/cisplatinum CT.

Despite the above approaches, new targets for the therapy of cancer as desired, in particular in the context of cellular functions mediated directly or indirectly by mTOR complex 1. It is therefore an object of the present invention, to provide these new targets and to employ these targets in the development of new and effective cancer therapies. Other objects and aspects of the present invention will become apparent to the person of skill upon reading the following description of the invention.

According to a first aspect thereof, the object of the present invention is solved by providing a method for identifying a compound that modulates the expression, the biological activity and/or the interaction of astrin with raptor in a cell, comprising the steps of a) contacting at least one of astrin, a raptor binding fragment of astrin, a cell expressing astrin, and/or a cell expressing a raptor binding fragment thereof with at least one compound that potentially modulates the expression, the biological activity and/or the interaction of astrin with raptor in a cell, and b) identifying a modulation of the expression and/or the binding of astrin or said fragment to raptor in the presence of said at least one compound.

It was surprisingly found by the present inventors that astrin provides a valuable tool for therapeutic approaches in order to treat or prevent cancer, as defective cell cycle progression in astrin deficient cells could limit astrin's suitability as therapeutic target. Nevertheless, astrin deficient mice (Xue, J., Tarnasky, H. A., Rancourt, D. E., and van Der Hoorn, F. A. (2002). Targeted disruption of the testicular SPAG5/deepest protein does not affect spermatogenesis or fertility. Mol Cell Biol 22, 1993-1997), and rats (Yagi, M., Takenaka, M., Suzuki, K., and Suzuki, H. (2007). Reduced mitotic activity and increased apoptosis of fetal sertoli cells in rat hypogonadic (hgn/hgn) testes. J Reprod Dev 53, 581-589) are viable, without displaying major phenotypes. Thus, the inventors found it conceivable to target astrin in human disease without affecting vital functions.

In the context of the present invention, the term "astrin" shall be understood as also indicating/representing the mammalian (in particular mouse) homolog of the human astrin gene and/or protein and/or mRNA. Also, the term shall comprise the complete astrin polypeptide or fragment as described herein, such as the raptor-binding fragment. The term also covers astrin in different preparations, such as in the cellular context, purified from the cell, or as part or associated with stress granules, and fractions thereof. Similarly, raptor shall be understood as also indicating/representing the mammalian (in particular mouse) homolog of the human raptor gene and/or protein and/or mRNA. Preferred is a method according to the present invention, wherein said modulation is selected from a decrease or an increase of said expression and/or of said binding to raptor.

Preferably, said identifying comprises a method selected from rtPCR, immunoprecipitation and measuring the induction or reduction of apoptosis in said cell. Respective assays are known to the person of skill.

More preferred is a method according to the present invention, wherein said compound is selected from the group consisting of a peptide library, a combinatory library, a cell extract, in particular a plant cell extract, a "small molecular drug", an antisense oligonucleotide, an siRNA, an mRNA and an antibody or fragment thereof specifically interfering with the binding of astrin to raptor.

According to the invention, said cell can be selected from the group of cancer cells, human non-embryonic stem cell recombinant host cells expressing astrin or the raptor binding fragment thereof, wherein said recombinant host cells optionally express raptor, yeast cells, and recombinant bacterial cells.

Further preferred is a method according to the present invention, wherein said raptor binding fragment of astrin comprises the N-terminal head domain of the astrin polypeptide, for example the N-terminal amino acids 1-481 of the astrin polypeptide as described herein, in particular in SEQ ID No. 1.

The method according to the present invention as described herein is thus suitable for the identification of compounds that can interact with the binding of astrin to raptor, and/or activities of astrin, and thus to identify, for example, inhibitors, competitors or modulators of the astrin function, in particular, inhibitors, competitors or modulators of the binding of astrin and/or its enzymatic activity. Preferred are compounds that inhibit the binding of astrin to raptor. Another aspect is directed at compounds that modulate the expression of astrin in a cell/in cells.

Another aspect is directed at a method according to the present invention, further comprising testing said compound(s) as identified for its activity to sensitise tumour cells to apoptosis. Since apoptosis occurs via a complex signaling cascade that is tightly regulated at multiple points, there are many opportunities to evaluate the activity of the proteins involved. A large number of apoptosis assays are devised to detect and count apoptotic cells. Apoptosis assays, based on methodology, can be classified into six major groups and include assays detecting cytomorphological alterations; DNA fragmentation; detection of caspases, cleaved substrates, regulators and inhibitors; membrane alterations; detection of apoptosis in whole mounts; and mitochondrial assays. One preferred assay is the microcul-ture-kinetic (MiCK) assay. Respective assays are known to the person of skill, ad can be taken from the respective literature.

The term "contacting" in the present invention means any interaction between the potentially binding substance(s) with astrin, whereby any of the two components can be independently of each other in a liquid phase, for example in solution, or in suspension or can be bound to a solid phase, for example, in the form of an essentially planar surface or in the form of part isles, pearls or the like. In a preferred embodiment a multitude of different potentially binding substances are immobilized on a solid surface like, for example, on a compound library chip and astrin (or a functional part thereof) is subsequently contacted with such a chip.

The astrin employed in a method of the present invention can be a full length protein or a fragment with N/C-terminal and/or internal deletions. Preferably the fragment is one that comprises the binding part of astrin to raptor and thus either an N-terminal fragment or a C-terminal fragment. Further preferred is a method according to the present invention, wherein said raptor binding fragment of astrin comprises the N-terminal head domain of the astrin polypeptide, for example the N-terminal amino acids 1-481 of the astrin polypeptide as described herein, in particular in SEQ ID No. 1.

The potentially binding substance, whose binding to astrin to be measured, can be any chemical substance or any mixture thereof. For example, it can be a substance of a peptide library, a combinatory library, a cell extract, in particular a plant cell extract, a "small molecular drug", a protein and/or a protein fragment.

Measuring of binding of the compound to astrin can be carried out either by measuring a marker that can be attached either to the protein or to the potentially interacting compound. Suitable markers are known to someone of skill in the art and comprise, for example, fluorescence or radioactive markers. The binding of the two components can, however, also be measured by the change of an electrochemical parameter of the binding compound or of the protein, e.g. a change of the redox properties of astrin or the binding compound, upon binding. Suitable methods of detecting such changes comprise, for example, potentiometric methods. Further methods for detecting and/or measuring the binding of the two components to each other are known in the art and can without limitation also be used to measure the binding of the potential interacting compound to astrin or astrin fragments. The effect of the binding of the compound or the activity of astrin can also be measured indirectly, for example, by assaying an enzymatic activity of astrin after binding.

As a further step after measuring the binding of a potentially interacting compound and after having measured at least two different potentially interacting compounds at least one compound can be selected, for example, on grounds of the measured binding activity or on grounds of the detected increase or decrease of astrin (binding) activity and/or expression.

Another aspect of the present invention thus involves a screening according to the present invention as described herein, further comprising an additional screening of the interaction of astrin with the stress granule component G3BP1. Said screening can either occur in the presence or absence of astrin, and in the presence or absence of a compound that has been identified (preselected) in a first screening using astrin and raptor as described herein.

The thus selected binding compound is then in a preferred embodiment modified in a further step. Modification can be effected by a variety of methods known in the art, which include without limitation the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, isopropyl, n-butyl, isobutyl, tert-butyl, n-pentyl or iso-pentyl groups, lower alkenyl groups, preferably having two to five carbon atoms, lower alkynyl groups, preferably having two to five carbon atoms or through the introduction of, for example, a group selected from the group consisting of $NH_2$, $NO_2$, OH, SH, NH, CN, aryl, heteroaryl, COH or COOH group.

The thus modified binding substances are than individually tested with a method of the present invention, i.e. they are contacted with astrin and subsequently binding of the modified compounds to the astrin polypeptide is measured. In this step, both the binding per se can be measured and/or the effect of the function of the astrin like, e.g. the binding to raptor and/or the enzymatic activity of the polypeptide can be measured. If needed the steps of selecting the binding compound, modifying the binding compound, contacting the binding compound with an astrin polypeptide and measuring the binding of the modified compounds to the protein can be repeated a third or any given number of times as required. The above described method is also termed "directed evolution" since it involves a multitude of steps including modification and selection, whereby binding compounds are selected in an "evolutionary" process optimizing its capabilities with respect to a particular property, e.g. its binding activity, its ability to activate or modulate the activity of the astrin polypeptide.

In view of the above, possible applications of the present invention for humans include:

a) Diagnostic approaches: Since astrin activity is linked with raptor and thus mTOR complex 1, genetic tests can be developed to assess an individual risk in relation to cancer based on astrin binding, activity and/or expression, in particular in order to develop a personalized treatment plan.

b) Pharmaceutical (cancer) and therapeutic approaches: The inventors' data indicate that an inhibition of the astrin action can be used as drug preventing, treating and/or slowing down the course of cancer in mammals/humans. An astrin binding inhibitor/inhibiting construct can be used as a cancer drug as well.

The astrin/raptor pathway defines a novel pathway with potentially valuable downstream targets that regulate cell division and apoptosis and/or other, yet unknown biological entities.

The term "homology" as used herein shall mean a value obtained by a BLAST [Basic local alignment search tool; Altschul, S. F. et al., J. Mol. Biol., 215, 403-410, (1990)] search. The homology in the amino acid sequence may be calculated by a BLAST search algorithm. More particularly, it may be calculated using a bl2seq program (Tatiana A. Tatusova and Thomas L. Madden, FEMS Microbiol. Lett., 174, 247-250, 1999) in a BLAST package (sgi32 bit edition, version 2.0.12; obtained from NCBI) in accordance with a default parameter. As a pairwise alignment parameter, a program "blastp" is used. Further, "0" as a Gap insertion cost value, "0" as a Gap elongation cost value, "SEG" as a filter for a query sequence, and "BLOSUM62" as a matrix are used, respectively.

According to another aspect thereof, the object of the present invention is solved by providing a screening tool for an agent for treating or preventing cancer, in particular a screening tool for screening for a compound that modulates the expression, the biological activity and/or the interaction of astrin with raptor in a cell, comprising an isolated cell expressing astrin, and/or expressing a raptor binding fragment thereof, wherein said cell optionally expresses raptor and/or an astrin binding fragment thereof, and wherein said cell is not a human embryonic stem cell. The cell can be a prokaryotic or eukaryotic cell, and the expression constructs can be present extrachromosomally or integrated into the chromosome. The polypeptides can be expressed in the form of a fusion protein, for example together with an enzymatically active moiety as reporter-construct, in order to be able to detect the expression product. Preferred host cells are derived from cells selected from the skeletal muscle, liver, adipose tissue, heart, pancreas, kidney, breast tissue, ovarian tissue, and/or hypothalamus. Thus, preferred is a screening tool according to the present invention, wherein said cell is selected from the group of cancer cells, recombinant host cells expressing astrin or the raptor binding fragment thereof, yeast cells, and recombinant bacterial cells, wherein said recombinant cell optionally expresses raptor and/or an astrin binding fragment thereof. Further preferred is a method according to the present invention, wherein said raptor binding fragment of astrin comprises the N-terminal head domain of the astrin polypeptide, for example the N-terminal amino acids 1-481 of the astrin polypeptide as described herein, in particular in SEQ ID No. 1.

According to yet another aspect thereof, the object of the present invention is solved by providing a screening tool for an agent for treating or preventing cancer, in particular a screening tool for screening for a compound that modulates the expression, the biological activity and/or the interaction of astrin with raptor in a cell, wherein said cell as above is part of a non-human transgenic mammal, which preferably overexpresses astrin and/or raptor optionally as a genetic reporter-construct. Preferred is a transgenic mouse, rat, pig, goat or sheep, wherein the reporter-construct is preferably expressed in cells selected from the skeletal muscle, liver, adipose tissue, heart, pancreas, kidney, and/or hypothalamus of said animal. Methods to produce these non-human transgenic mammal overexpressing astrin and/or raptor and/or carrying a astrin and/or raptor genetic reporter-construct are well known to the person of skill in the art. Preferred are also transgenic non-human mammals wherein the gene that is homologous to astrin/raptor is exchanged by a gene having a modified function (e.g. knockout or knock-in animal).

Similar to the strategies for identifying compounds that interact with astrin and the binding thereof to raptor, and/or the biological activity of astrin, compounds can be identified that modulate the expression of astrin in a cell. In preferred strategies, the expression of astrin can be monitored using a genetic reporter-construct for astrin (order to analyse the translation efficiency and/or stability of the astrin polypeptide), for an example a fusion protein comprising a detectable fusion member (such as an enzymatic or fluorophoric group, or GFP as described herein), or the amount of mRNA as present in a cell can be measured, for example, by Northern blot. The expression can also be analysed and monitored by using chip-analysis or rtPCR. Preferred compounds that modulate the expression of astrin in a cell are selected from specific antisense oligonucleotides, siRNAs, mRNAs or other preferably mutated nucleic acids encoding astrin. These genetic elements can be used in order to provide/maintain the loss-of-function (e.g. by the truncations as identified) of astrin, or the raptor binding thereof, in said cell. Another preferred embodiment is the transfer of said genetic elements using gene therapy. Furthermore, encompassed are viral constructs for the introduction of said genetic elements into said cells. Alternatively, also the "naked" nucleic acid can be introduced into the cell(s), e.g. by using particle-mediated technologies. Respective methods are well described in the literature and known to the person of skill.

Further preferred is the screening tool according to the present invention as described herein, wherein said astrin and/or raptor and/or the fragments thereof are labeled. Labels and methods for labeling are known to the person of skill, and can be enzymatic labels, dyes, fluorophores, and/or radioactive labels.

According to yet another aspect thereof, the present invention relates to the use of the tools according to the present invention as described herein for screening for a compound that modulates the expression, the biological activity and/or the interaction of astrin with raptor in a cell as described herein. Preferred is a use according to the present invention, wherein said tool is a raptor binding fragment of astrin comprising the N-terminal head domain of the astrin polypeptide, for example the N-terminal amino acids 1-481 of the astrin polypeptide as described herein, in particular in SEQ ID No. 1.

Another aspect of the present invention relates to a method for manufacturing a pharmaceutical composition for treating or preventing cancer, comprising the steps of: performing a screening method according to the present invention, and formulating said compound as screened and identified into a pharmaceutical composition.

In a further embodiment of the method of the present invention, the interacting compound identified as outlined above, which may or may not have gone through additional rounds of modification and selection, is admixed with suitable auxiliary substances and/or additives. Such substances comprise pharmacological acceptable substances, which increase the stability, solubility, biocompatibility, or biological half-life of the interacting compound or comprise substances or materials, which have to be included for certain routs of application like, for example, intravenous solution, sprays, band-aids or pills.

Carriers, excipients and strategies to formulate a pharmaceutical composition, for example to be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form are well known to the person of skill and described in the respective literature.

Administration of an agent, e.g., a compound can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

Yet another aspect of the present invention is directed at a pharmaceutical composition for treating or preventing cancer, obtainable by a method according to the method as above.

In certain embodiments, the compound (inhibitor) is administered to the subject by administering a recombinant nucleic acid, such as, for example, an anti-astrin RNA, for example an si-RNA. Preferably, the recombinant nucleic acid is a gene therapy vector.

Another aspect of the present invention relates to a method or use as described herein, wherein the pharmaceutical composition further comprises additional pharmaceutically active ingredients for treating cancer, i.e. chemotherapeutics, such as, for example, rapamycin.

Another aspect of the present invention then relates to a method for treating or preventing cancer in a patient, comprising administering to said patient an effective amount of a pharmaceutical composition according to the invention as above. In general, the attending physician will base a treatment on the compound as identified, and optionally also on other individual patient data (clinical data, family history, DNA, etc.), and a treatment can also be performed based on the combination of these factors. This method of the present invention for example involves integrating individual diagnostic cancer data with patient clinical information and general healthcare statistics to enable, for example, the application of personalized medicine to the patient. Significant information about drug effectiveness, drug interactions, and other patient status conditions can be used, too.

Preferred is a therapeutic method according to the present invention, wherein said mammal to be treated is a mouse, rat or human.

More preferably, the cancer to be treated is a solid tumor, such as, for example, selected from breast, bone, ovarian, liver, kidney, and lung cancer.

Preferably, an inhibiting active agent is administered in form of a pharmaceutical composition, such as an antibody, nucleotide or an inactivating binding compound for the astrin/raptor binding. Preferably, said patient is a human being. Treating is meant to include, e.g., preventing, treating, reducing the symptoms of, or curing the disease or condition, i.e. cancer.

Another aspect of the present invention then relates to the use of a modulator of the binding of astrin to raptor, and/or the expression and/or the biological activity of astrin in a cell for the manufacture of a pharmaceutical composition for treating or preventing cancer. Preferred is a use according to the present invention, wherein said modulator is an inhibitor of the binding of astrin to raptor and/or the expression and/or biological activity of astrin.

Another aspect of the present invention then relates to a monoclonal antibody or a functional fragment thereof (such as, for example, an scFv or Fab fragment) that specifically recognizes and interacts with the binding of astrin to raptor. Preferably, said monoclonal antibody or a functional fragment thereof interferes (such as inhibits) the binding of astrin to raptor. The antibodies or fragments thereof can also be labeled (see above), and/or carry a therapeutic group attached to them, such as, for example, for antibody-directed enzyme prodrug therapy (ADEPT) or radioimmunotherapy (RIT).

An "effective amount" is an amount of the compound(s) or the pharmaceutical composition as described herein that reduces on the expression and/or abundance of astrin, or inhibits and/or reduces the binding of astrin to raptor. The amount alleviates symptoms as found for cancer. Alleviating is meant to include, e.g., preventing, treating, reducing the symptoms of, or curing the disease (cancer) or condition (e.g. tumor size and/or metastases.

The invention also includes a method for treating a subject at risk for cancer, wherein a therapeutically effective amount of a modulator as above is provided. Being at risk for the disease can result from, e.g., a family history of the disease, a genotype which predisposes to the disease, or phenotypic symptoms which predispose to the disease. A further aspect of the present invention is the use of a modulator of the expression and/or the biological activity of astrin, and/or the binding of astrin to raptor in a cell for the manufacture of a pharmaceutical composition for treating or preventing cancer. Preferably, said modulator is an inhibitor of the expression and/or biological activity and/or the binding of astrin to raptor as described herein.

As mentioned above, the mammalian target of rapamycin (mTOR) kinase is a central regulator of cellular growth and metabolism (Polak, P., and Hall, M. N. (2009). mTOR and the control of whole body metabolism. Curr Opin Cell Biol 21, 209-218). mTOR is deregulated in a large number of tumours and age-related disorders (Laplante, M., and Sabatini, D. M. (2012). mTOR Signaling in Growth Control and Disease. Cell 149, 274-293), and mTOR inhibitors are currently in clinical studies for tumour and metabolic diseases (Inoki, K., Kim, J., and Guan, K. L. (2012). AMPK and mTOR in cellular energy homeostasis and drug targets. Annu Rev Pharmacol Toxicol 52, 381-400).

mTOR occurs in two distinct multiprotein complexes, named mTOR complex 1 (mTORC1) and mTORC2. Translational control by mTORC1 occurs at several levels, short term by regulation of several translation initiation factors including 4E binding protein (4E-BP1), and long term by controlling translation of ribosomal components, and by processing of pre-rRNA (Grzmil, M., and Hemmings, B. A. (2012). Translation regulation as a therapeutic target in cancer. Cancer Res 72, 3891-3900; Iadevaia, V., Wang, X., Yao, Z., Foster, L. J., and Proud, C. G. (2012a). Evaluation of mTOR-regulated mRNA translation. Methods Mol Biol 821, 171-185; Iadevaia, V., Zhang, Z., Jan, E., and Proud, C. G. (2012b). mTOR signaling regulates the processing of pre-rRNA in human cells. Nucleic Acids Res 40, 2527-2539; Thedieck, K., and Hall, M. N. (2009). Translational Control by Amino Acids and Energy. In The Handbook of Cell Signaling, R. B. a. E. Dennis, ed., pp. 2285-2293).

Oxidative stress and ROS induce stress granules (SGs) and p-bodies (PBs), which are highly dynamic, microtubuli dependent structures that regulate mRNA turnover and translation and contribute to cell survival (reviewed by Thomas et al. (Thomas, M. G., Loschi, M., Desbats, M. A., and Boccaccio, G. L. (2011). RNA granules: the good, the bad and the ugly. Cell Signal 23, 324-334; and Anderson, P., and Kedersha, N. (2009b). Stress granules. Curr Biol 19, R397-398)). SGs and PBs are evolutionary conserved RNA granules. They are in constant exchange with each other and share several components including the PB and SG marker protein p54/DDX6. PBs are constitutive cellular components, and are sites of mRNA decay via miRNA, RNAi, or nonsense mediated decay. In contrast, SGs are sites of mRNA storage that are formed under stress. The cellular response to temperature, nutrient stress, oxidative stress, or irradiation activates several mechanisms for translational repression, among them eIF2alpha-S51 phosphorylation and inhibition, leading to accumulation of non-polysomal polyadenylated mRNA and translation initiation factors within RNA granules. These mRNA-protein complexes can assemble in SGs, together with self-associating SG components, including the cytotoxic granule-associated RNA binding protein TIA1, the TIA-1 related protein TIAR, and the RasGAP SH3-binding protein G3BP1. Notably, overexpression of these latter components is often sufficient to induce SGs. mRNAs in SGs are sorted for decay in PBs, or stored for translation reinitiation upon stress relief.

Although both SGs and mTOR are closely connected to redox stress and translational regulation, there is no evidence of connections between the two in mammals, and the direct molecular links remain elusive. In the present invention, the inventors establish astrin as a critical component of mTORC1 signalling, which couples mTORC1 activity with SG assembly and apoptosis susceptibility of cancer cells. They could demonstrate that astrin recruits the mTORC1 component raptor to SGs and dissociates the mTOR-raptor complex to limit mTORC1 activation upon metabolic challenge and redox stress induction. Furthermore, the data indicates that astrin mediates mTORC1-dependent anti-apoptotic SG functions. As astrin is highly expressed in cancer cells, and hypoxia induced redox stress is a common condition in tumours, astrin is a promising target for therapeutic intervention to control mTORC1 activity and sensitise tumour cells to apoptosis.

The following figures, sequences, and examples merely serve to illustrate the invention and should not be construed to restrict the scope of the invention to the particular embodiments of the invention described in the examples. All references as cited herein are hereby incorporated in their entirety by reference.

SEQ ID NO 1 shows the amino acid sequence of human astrin.

FIG. 1 schematically shows that astrin is induced and the NFL is inhibited in aggressive breast and lung tumor cell lines FIG. 2 shows binding of astrin to raptor.

EXAMPLES

Experimental Procedures

Figure 1:
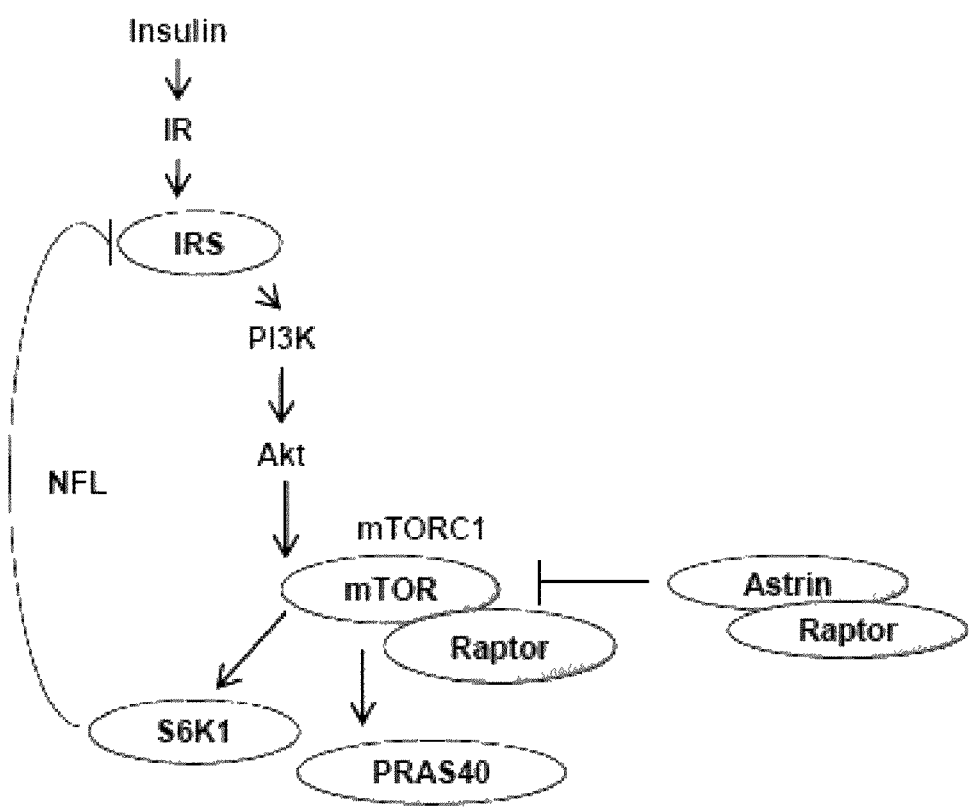

Constructs, Reagents, Cell Lines, and Tissue Culture.

pCMV6-AC-FLAG-astrin (order # RC201783) was purchased from Origin, Rockville, Md., USA. The astrin full length cDNA sequence was transferred into the following plasmids according to the manufacturer's protocol: pCMV6-AC-GFP, pCMV6-AN-GFP, pCMV6-AN-FLAG, pCMV6-entry. DNA transfections were done with JetPEI, PolyPlus, Strasbourg, France as described (Sonntag, A. G., Dalle Pezze, P., Shanley, D. P., and Thedieck, K. (2012). A modelling-experimental approach reveals IRS dependent regulation of AMPK by Insulin. FEBS J).

siRNA transfection was done with Lipofectamine™ 2000, Invitrogen, Carlsbad, Calif., USA according to the manufacturers protocol. Astrin/SPAG5 siRNA (order #L-006839-00-0005) was obtained from Dharmacon ThermoFisherScientific, Waltham, Mass., USA. Stably transduced inducible shRNA cell lines for raptor and TSC2 have been described (Dalle Pezze et al., 2012b). Astrin siRNA was induced with ON-TARGET plus SMARTpool siRNA (#L006839-00-0005), Thermo Fisher Scientific, Waltham, Mass., USA.

Lentiviral astrin shRNA (order #RHS4740) was obtained from Open Biosystems, Thermo Fisher Scientific, Waltham, Mass., USA as inducible shRNAmir gene set. HeLa α Kyoto cells were transduced with lentivirus according to the manufacturers protocol (clone A8, ID#V2THS_203559; G9, ID#V2THS_203218; D9, ID#V3THS_361123; H8, ID#V3THS_361121; B1, ID#V3THS_361120). Target sequences for all siRNAs and shRNA clones were different.

Experiments were performed in HeLa α Kyoto cells, and BT474, MDA-MB-231, MDA-MB-453, T-47D, MCF-7 breast cancer cell lines. Tissue culture protocols were described (Dalle Pezze, P., Sonntag, A. G., Thien, A., Prentzell, M. T., Godel, M., Fischer, S., Neumann-Haefelin, E., Huber, T. B., Baumeister, R., Shanley, D. P., et al. (2012b). A Dynamic Network Model of mTOR Signaling Reveals TSC-Independent mTORC2 Regulation. Sci Signal 5, ra25). Cultivation of breast cancer cell lines T-47D, BT474, MDA-MB-231 and MDA-MB-453 was done in the following media: RPMI (PAA, Pasching, Austria) supplemented with 100 nM insulin. MCF7 cells were cultivated in RPMI (PAA, Pasching, Austria). Insulin/aa induction was done as described (Sonntag et al., 2012). Prior to stress induction with 500 μM Arsenite or 2 mM $H_2O_2$, cells were starved for 16 h in DMEM without Glucose and fetal calf serum (PAA, Pasching, Austria) supplemented with 1.5% L-glutamine.

Stress granules were analysed after 30 min. stress induction. Apoptosis was analysed after 1-3 hours stress induction. Inhibitors were obtained from Calbiochem, Merck KGaA, Darmstadt, Germany and Sigma Aldrich, St. Louis, USA; dissolved in DMSO, and applied 30 min. prior to all induction regimens, at the following concentrations: Rapamycin (100 nM), PP242 (250 nM), Wortmannin (200 nM), Cycloheximide (2 μg/mL); HeLa cells were synchronized with Nocodazole (400 ng/mL) and subsequent mitotic shake off at G2/M, and released as described (Thein, K. H., Kleylein-Sohn, J., Nigg, E. A., and Gruneberg, U. (2007). Astrin is required for the maintenance of sister chromatid cohesion and centrosome integrity. J Cell Biol 178, 345-354).

Mass Spectrometry.

Identification of novel mTOR and raptor interactors was performed as described (Thedieck, K., Polak, P., Kim, M. L., Molle, K. D., Cohen, A., Jeno, P., Arrieumerlou, C., and Hall, M. N. (2007). PRAS40 and PRR5-like protein are new mTOR interactors that regulate apoptosis. PLoS One 2, e1217007).

Lysis, IP and immunoblotting (IB) were described elsewhere (Dalle Pezze, P., Sonntag, A. G., Shanley, D. P., and Thedieck, K. (2012a). Response to Comment on "A Dynamic Network Model of mTOR Signaling Reveals TSC-Independent mTORC2 Regulation". Sci Signal 5; Dalle Pezze et al., 2012b; Sonntag et al., 2012; Thedieck et al., 2007). Antibodies are described elsewhere (Dalle Pezze et al., 2012b; Sonntag et al., 2012). Further antibodies were from Bethyl, Montgomery, Tex., USA against Histone H3 (#A300-823A), Histone H3-p 510 (#A301-844A), and DDX6/p54 (#A300-461A); from Cell Signaling Technology Inc., Boston, Mass., USA against ATF-4 (#11815), hnRNP-A1 (#8443), YB1 (#9744), HSP90 (#4877), HSP70 (#4867), HSF1 (#4356); from Santa Cruz, Calif., USA against G3BP1 (#sc-81940), astrin (#sc-98605); and from Abcam, Cambridge, UK against Plk1 (#ab17056). All antibodies were used according to the manufacturers' instructions. Monoclonal antibodies for PLA were generated in mice or rats for astrin, mTOR, and raptor by Dr. Elisabeth Kremmer, Helmholtz Zentrum München, Institute of Molecular Immunology, Marchioninistrasse 25, 81377 Munich, Germany. Peptides for antibody raising were made by Peptide Specialty Laboratories (PSL) GmbH, Heidelberg, Germany.

IF, Fluorescence Microscopy, and Confocal Microscopy.

IF stainings were performed as described (Thedieck et al., 2007). Cells were fixed for 5 min. with ice cold methanol at −20° C. GFP-transfected cells were fixed with 4% paraformaldehyde for 20 min. at room temperature. Fluorescence microscopy was performed with an Axioimager.Z1 compound microscope with an AxioCam MRm3 CCD camera; Axiovision software version 4.8.1 (Carl Zeiss AG, Germany) was used for image analysis. Confocal imaging was performed with a LSM 510 Duo-Live microscope equipped with a 100×/1.45 NA Plan-Apochromate objective (both Carl Zeiss). Excitation of the fluorophores (Hoechst 33342, Alexa-488, Cy3, Cy5) was performed at 405, 488, 561, and 633 nm respectively. For detection of the emission signal at specified ranges, the photomultiplier channels were used with BP filter 420-480, BP 505-530, BP 575-615, LP 650 nm. Confocal pinhole diameters were always adjusted to 1 μm sections. Scale bars in all images are 10 μm.

PLA Analysis.

All reagents used for PLA analysis were from Olink Bioscience, Uppsala, Sweden, and all PLA reactions were performed following the manufacturer's instructions in a dark humidity chamber with a sample volume of 20 μL per well. Briefly, cells were seeded on Teflon coated PLA slides (Menzel-Glaser, Thermo Scientific) and cultured for two days at 37° C. in 7.5% $CO_2$. Cells were fixed with 100% Methanol −20° C. for 5 min. After fixation cells were treated with 0.5% Saponin in PBS for 15 minutes at 4° C. and 15 minutes at RT, and blocked in 5% BSA in PBS for 60 minutes at 37° C. Cells were incubated with primary antibodies (self made against mTOR complex components and astrin, 1:50 dilution in antibody diluent) overnight at 4° C. Next day, cells were incubated with the according PLA probes (secondary antibodies conjugated to unique DNA probes for anti-mouse, anti-rabbit, or anti-rat, respectively) for 60 minutes at 37° C. For ligation and circularization of the DNA-oligos, cells were incubated with ligase-solution for 30 minutes at 37° C. For rolling circle amplification cells were incubated with amplification-solution, containing a complementary Alexa 555-labeled DNA linker as detectable fluorophore for 120 minutes at 37° C. Cells were mounted with a cover slip (24×50 mm) using a minimal volume of Duolink In Situ Mounting Medium with DAPI and analyzed by confocal microscopy (Zeiss LSM 510 or LSM 780 META laser scanning microscope equipped with a 63×/1.4 oil DIC objective), (Zeiss, Jena, Germany). Pictures were taken with optimal frame size of 1024×1024 (1764×1764) pixels, scan speed 7 for superior images and with dynamic range of 12 bit (8 bit). Amplifier offset and detector gain were adjusted first and never changed for an experimental session. The signal-per-cell ratio (numbers of red PLA spots per cell) was analyzed with the freely distributed BlobFinder software (Centre for Image Analysis, Uppsala University, Sweden) which counts PLA-signals and nuclei as defined pixel-size for each individual cell.

Quantitations and Statistics.

All experiments were performed in at least N=3 replicates. Signals in IBs were quantified and normalised as described (Dalle Pezze et al., 2012b). For analysis of IB and PLA data, non-parametrical two tailed student's t-test was used assuming unequal variances. Statistical analysis was performed with a confidence interval of p<0.05. The Standard Error of the Mean (SEM) was chosen to estimate the statistical variability. Box and whisker plots were computed with the GraphPad Prism 6.01 software. Percentiles were calculated according to the following formula: Result=percentile*[n(values)+1/100]. Indicated is the median ($50^{th}$ percentile), the $25^{th}$ to $75^{th}$ percentile (box), and the $5^{th}$ to $95^{th}$ percentile (whiskers).

Astrin is a Specific Raptor Interactor which Inhibits mTORC1 Assembly

To identify novel mTOR regulators, the inventors immunopurified endogenous mTOR, raptor (mTORC1), and Rictor (mTORC2) from HeLa cells and analysed the immunprecipitates (IPs) by mass spectrometry (MS) as described (Thedieck et al., 2007). Strikingly, although raptor is generally thought to act in complex with mTOR (Laplante, M., and Sabatini, D. M. (2012). mTOR Signaling in Growth Control and Disease. Cell 149, 274-293), the inventors identified astrin in raptor IPs (FIG. 2, sequence coverage 12%), but not mTOR or Rictor IPs. This suggested that astrin binds to raptor, when the latter is not in a complex with mTOR (mTORC1).

Astrin (UniProtKB: Q96R06) is a large protein of 160 and 140 kDa, the smaller isoform possibly arising from proteolytic cleavage. High astrin mRNA levels correlate with negative prognosis in breast and lung cancer (Buechler, S. (2009). Low expression of a few genes indicates good prognosis in estrogen receptor positive breast cancer. BMC Cancer 9, 243; Valk, K., Vooder, T., Kolde, R., Reintam, M. A., Petzold, C., Vilo, J., and Metspalu, A. (2010). Gene expression profiles of non-small cell lung cancer: survival prediction and new biomarkers. Oncology 79, 283-292). Therefore, the inventors analysed astrin protein expression in three breast cancer cell lines. Astrin protein levels positively correlated with Akt activity, and negatively correlated with phosphorylation of the mTORC1 substrates PRAS40-S183 and p70-S6K1-T389.

Figure 2:
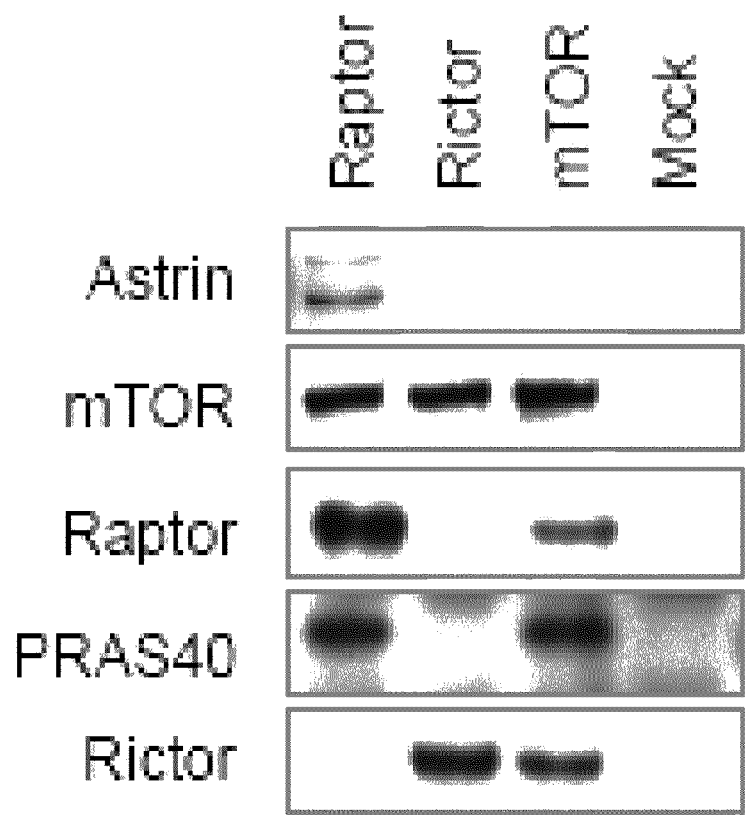
Figure 3:
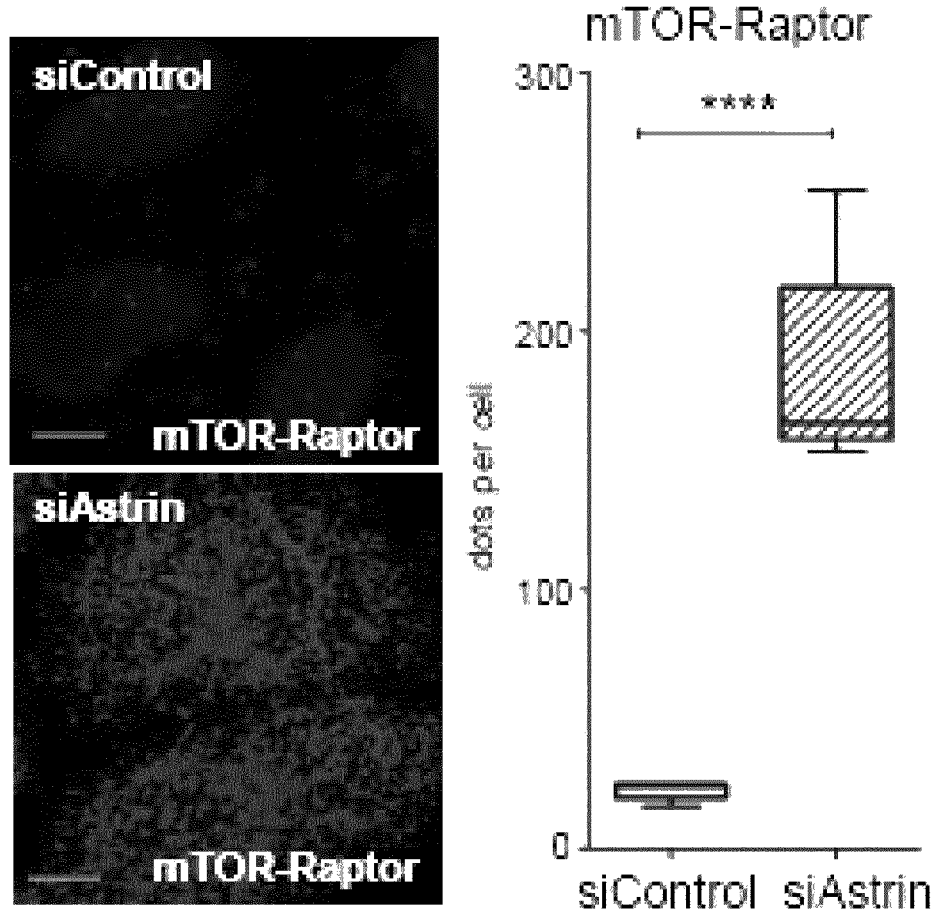
FIG. 3 shows that astrin deficiency induces mTOR complex 1.
Figure 4:
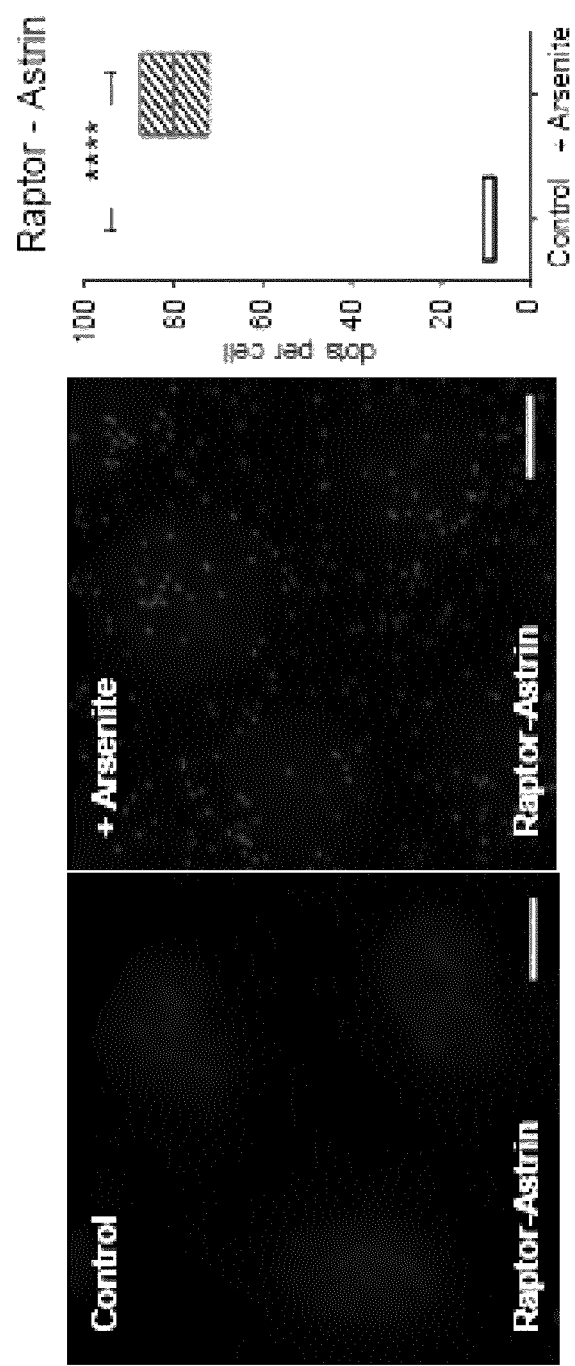
FIG. 4 shows that arsenite induces stress and subsequent astrin-raptor binding.

Overexpression of FLAG-astrin in HeLa cells increased the level of raptor strengthening the notion of a possible functional connection between astrin and raptor. FLAG-astrin coimmunoprecipitated with raptor, but not with mTOR or the mTORC2 component Rictor, confirming the MS data. Also, endogenous astrin co-immunopurified with raptor, but not with mTOR (FIG. 2). Thus, astrin is a specific interactor of the essential mTORC1 component raptor, but not of mTOR kinase itself. Upon incubation of cells with the allosteric mTORC1 inhibitor Rapamycin for 30 minutes followed by IP, raptor was observed to dissociate from the mTOR-raptor-complex, but no effect on astrin-raptor binding was seen. Thus, mTORC1 activity does not affect raptor-astrin binding. In contrast, astrin inhibition affects mTORC1 assembly, as siRNA knockdown of astrin resulted in increased mTOR amounts in raptor IPs. Likewise, in situ measurement of mTOR-raptor association by proximity ligation assay (PLA) (Soderberg, O., Leuchowius, K. J., Gullberg, M., Jarvius, M., Weibrecht, I., Larsson, L. G., and Landegren, U. (2008). Characterizing proteins and their interactions in cells and tissues using the in situ proximity ligation assay. Methods 45, 227-232) revealed drastic induction of mTORC1 assembly upon astrin knockdown (FIGS. 3 and 4). The inventors conclude that astrin competes with mTOR for raptor binding, resulting in increased mTORC1 formation in the absence of astrin.

Astrin Inhibits mTORC1 Signalling

Astrin has been described as a regulator of mitotic progression, and for mTORC1 a role in mitosis has been proposed. The inventors therefore tested if astrin deficiency alters mTORC1 activity during mitosis. In HeLa cells arrested at G2/M with Nocodazole and—upon release from the mitotic block—a phosphorylation of the mTORC1 substrate p70-S6K1-T389 was observed. p70-S6K1-T389 was only weakly phosphorylated in mitotic cells, and remained unaltered upon astrin inhibition. In contrast to mitotic cells, astrin deficiency induced p70-S6K1-pT389 in non-synchronised cells, suggesting a regulatory role of astrin toward mTORC1 outside of mitosis. Astrin deficiency in non-synchronised cells induces phosphorylation of the mTORC1 substrate p70-S6K1-T389, and this effect is independent of astrin's mitotic functions. To further establish the role of astrin in mTORC1 signalling, the inventors starved and induced cells with insulin and aa for 10 minutes to strongly activate mTOR signalling with and without astrin knockdown; and confirmed p70-S6K1-pT389 induction in astrin deficient cells. The mTORC1 specific inhibitor Rapamycin and the ATP-analogue inhibitor PP242 (targeting both mTOR complexes) both potently inhibited p70-S6K1-pT389 in astrin deficient cells. Thus, astrin's inhibitory effect on p70-S6K1-pT389 is mTORC1-dependent.

Activated p70-S6K1 inhibits IRS1 by phosphorylation at S636/639 (i.e. the NFL). In line with activated mTORC1 and p70-S6K1 upon astrin deficiency, the inventors found that IRS-pS636/639 was induced by astrin siRNA. Time-course experiments upon insulin/aa induction revealed that astrin deficiency accelerates the phosphorylation induction of the mTORC1 substrates p70-S6K1-T389 and PRAS40-S183 mTORC1, and of the p70-S6K1 substrate IRS1-S636/639 (5 minutes post induction in siAstrin versus 7 minutes in control cells, respectively). siAstrin also accelerated the onset of the NFL and resulting suppression of p70-S6K1-pT389 (decline at 7 minutes post induction in siAstrin cells, as compared to steady state induction up to 20 minutes post induction in control cells). Thus, overall mTORC1 network dynamics are accelerated in the absence of astrin. A scheme on mTORC1 regulation by astrin is depicted in FIG. 1.

The Astrin-Raptor Complex Localises to Stress Granules (SGs)

Figure 5:
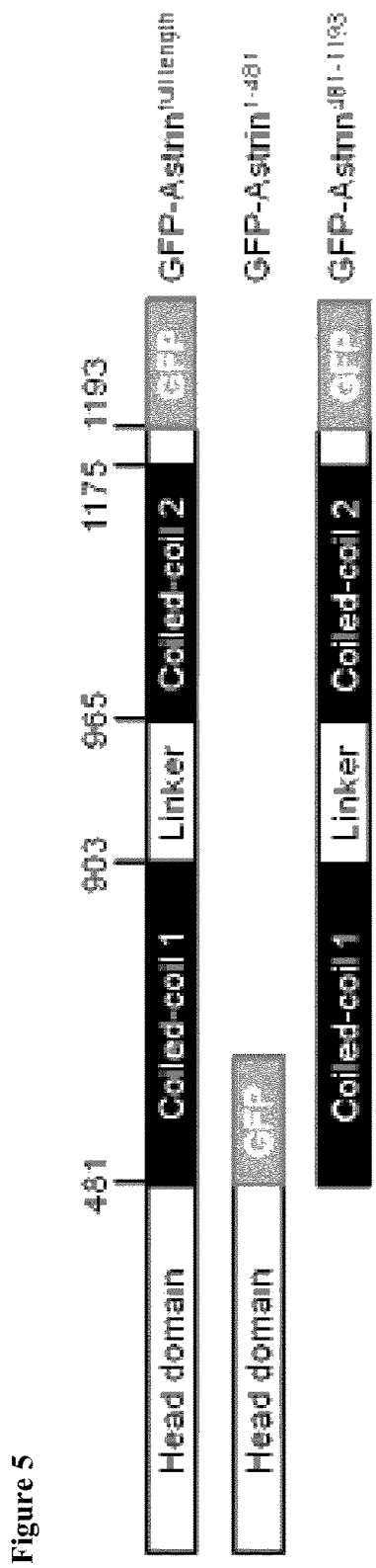
FIG. 5 shows astrin-constructs as used in the context of the present invention, and for use as screening tools.

To further address the biological function of the astrin-raptor interaction, the inventors generated recombinant astrin-GFP fusion constructs. The modular structure of astrin with its N-terminal globular head domain and the two C-terminal coiled-coil domains (Gruber, J., Harborth, J., Schnabel, J., Weber, K., and Hatzfeld, M. (2002). The mitotic-spindle-associated protein astrin is essential for progression through mitosis. J Cell Sci 115, 4053-4059) suggested that astrin may serve as an adaptor protein. The inventors thus generated constructs for full length astrin (GFP-astrin$^{full\ length}$), the N-terminal head domain (GFP-Astrin$^{1-481}$), and the C-terminal coiled-coil domains (GFP-astrin$^{482-1193}$) (scheme depicted in FIG. 5).

GFP-astrin$^{full\ length}$ localised into cytoplasmic granular structures that were also visible by light microscopy. Of note, also the C-terminal GFP-astrin$^{482-1193}$ localised to cytosolic granular structures, whereas the N-terminal GFP-astrin$^{1-481}$ showed a diffuse cytosolic localisation. In contrast, GFP-astrin$^{full\ length}$ and the N-terminal GFP-astrin$^{1-481}$ co-purified with raptor, whereas the C-terminal GFP-astrin$^{482-1193}$ only weakly associated with raptor. These data are in line with astrin's N-terminal head domain primarily mediating raptor binding, whereas astrin's C-terminal coiled-coil domains primarily mediate its localisation. mTOR or astrin binding to raptor are mutually exclusive.

To analyse if endogenous astrin localises to SGs, the inventors induced oxidative stress in HeLa cells for 30 minutes with 500 µM Arsenite. Arsenite induces a large variety of cellular ROS (Jomova, K., Jenisova, Z., Feszterova, M., Baros, S., Liska, J., Hudecova, D., Rhodes, C. J., and Valko, M. (2011). Arsenic: toxicity, oxidative stress and human disease. J Appl Toxicol 31, 95-107). The commercial astrin antibody as used detected astrin-GFP in immunofluorescence (IF), confirming its specificity. In non-stressed cells endogenous astrin showed a microtubuli pattern. The specific SG marker G3BP1 localised into granular cytoplasmic structures, i.e. SGs upon Arsenite stress, and astrin partially co-localised with G3BP1, thus astrin localises to SGs upon Arsenite stress. HA-raptor co-localised with astrin and G3BP1 into SGs. In contrast, mTOR did not co-localise with G3BP1. Thus, upon oxidative stress, astrin and raptor co-localise with SGs, whereas mTOR remains excluded from SGs. These findings led the inventors to hypothesise that re-localisation of the astrin-raptor complex to SGs might disassemble the mTOR-raptor complex under oxidative stress. In agreement with an astrin-raptor complex being formed and relocalising to SGs under stress, astrin association with raptor was strongly increased by Arsenite in co-IPs and in situ (FIG. 4). Thus, formation of the raptor-astrin complex and its association with SGs is induced by Arsenite stress.

It was then tested if these effects are specific to Arsenite, or could be also observed with other oxidative, SG-inducing stresses. Hydrogen peroxide (H$_2$O$_2$) induces SGs. Therefore the above described experiments were repeated with 2 mM H$_2$O$_2$. All results with H$_2$O$_2$ reproduced those obtained with Arsenite, and thus different oxidative stresses induce astrin mediated recruitment of raptor to SGs, leading to mTORC1 disassembly.

Figure 6:
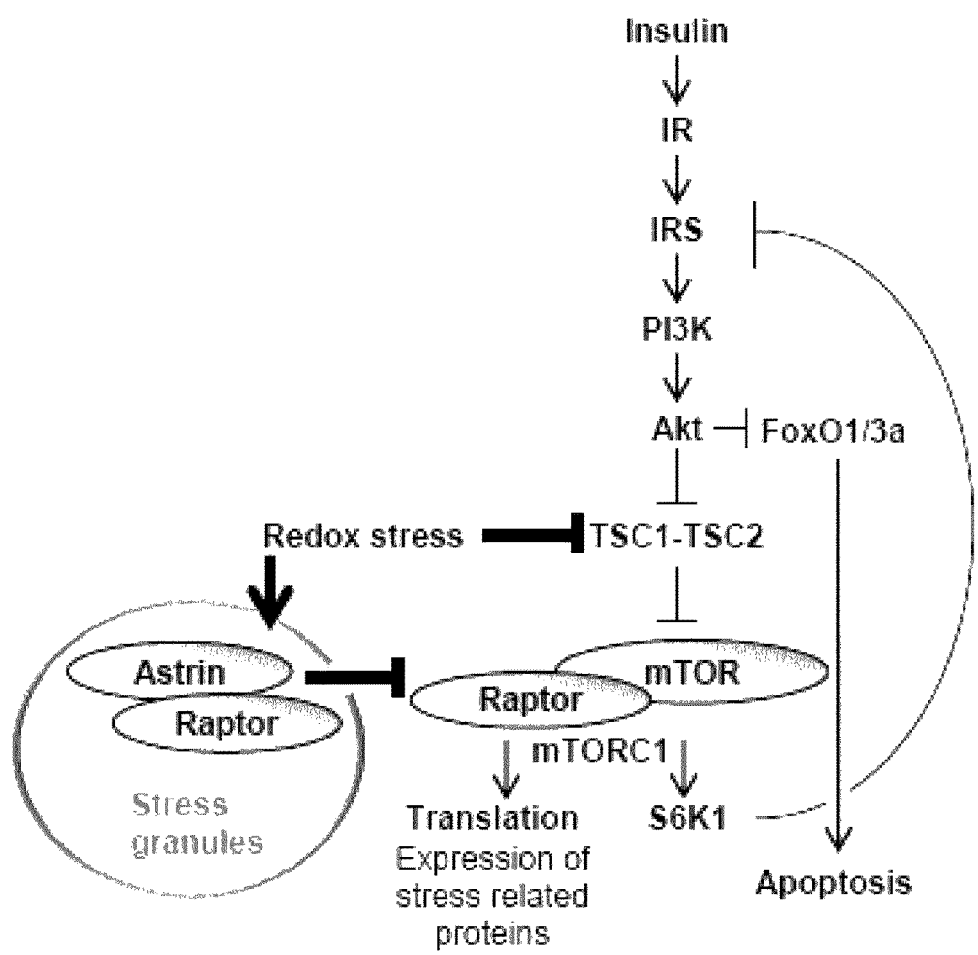
FIG. 6 shows the findings as used in the context of the present invention in an overview.

SG and Astrin Dependent mTORC1 Repression Protects Cancer Cells from Oxidative Stress Induced Apoptosis For the medical implications of the present findings, high astrin levels correlate with cancer cell aggressiveness (Buechler, 2009; Valk et al., 2010), as well as high Akt and low mTORC1 signalling in breast tumour cells. Redox stress due to hypoxia is a common condition in tumours, and tumour cells need to evade apoptosis in response to oxidative insults (Fruehauf, J. P., and Meyskens, F. L., Jr. (2007). Reactive oxygen species: a breath of life or death? Clin Cancer Res 13, 789-794; Sosa et al., 2012). In line, chemoresistance of cancer cells often relies on their increased capacity to suppress apoptosis (Ajabnoor, G. M., Crook, T., and Coley, H. M. (2012). Paclitaxel resistance is associated with switch from apoptotic to autophagic cell death in MCF-7 breast cancer cells. Cell Death Dis 3, e260). Although active mTOR is generally thought to promote cell growth and thereby inhibit apoptosis, hyperactive mTORC1 signalling sensitises cells to apoptosis (Thedieck et al., 2007). Interestingly, astrin deficiency facilitates apoptosis, and the inventors found that siAstrin sensitised HeLa cells to H$_2$O$_2$ induced apoptosis, as measured by cleaved PAR). Importantly, astrin dependent apoptosis induction was inhibited by shRaptor mediated mTORC1 inhibition, and the inventors conclude that mTORC1 suppression by astrin protects HeLa cells under oxidative stress against apoptosis. These findings also translate to other cancer cells as was shown in several breast cancer cell lines, such as MCF-7 breast cancer cells. In summary, astrin inhibits apoptosis in cancer cells by preventing mTORC1 hyperactivation under oxidative stress (see FIG. 6).

In the context of the present invention, astrin and its interaction with raptor were identified as novel critical components of the mTORC1 network. Astrin recruits raptor to SGs, leading to mTORC1 disassembly which limits mTORC1 activity under conditions that induce mTORC1, including nutrient and insulin stimulation as well as oxidative and heat stress. The present invention unravels astrin as the key link that dissociates mTORC1 and limits its activity in metabolically challenged cells. Inhibition of either astrin or SGs under transient stress causes cells to undergo apoptosis due to mTORC1 hyperactivation, underlining the critical importance of astrin and SGs in limiting mTORC1 activity. The mTORC1 inhibitor Rapamycin extends life span (Harrison, D. E., Strong, R., Sharp, Z. D., Nelson, J. F., Astle, C. M., Flurkey, K., Nadon, N. L., Wilkinson, J. E., Frenkel, K., Carter, C. S., et al. (2009). Rapamycin fed late in life extends lifespan in genetically heterogeneous mice. Nature 460, 392-395) and prevents cancer development (Anisimov, V. N., Zabezhinski, M. A., Popovich, I. G., Piskunova, T. S., Semenchenko, A. V., Tyndyk, M. L., Yurova, M. N., Antoch, M. P., and Blagosklonny, M. V. (2010). Rapamycin extends maximal lifespan in cancer-prone mice. Am J Pathol 176, 2092-2097). Thus ROS-mediated mTORC1 activation may be important for normal cellular function, and may also be involved in ageing and cancer development. Our data support this dual role, as astrin depletion and the resulting mTORC1 hyperactivation foster cell death under transient stress, but increased astrin levels are positively correlated with cancer progression (Buechler, 2009; Välk et al., 2010).

One effect of astrin mediated mTORC1 inhibition is the inactivation of the mTORC1-dependent NFL toward Akt. Akt activation results in increased FoxO1/3A phosphorylation and inactivation, a mechanism which is well known to prevent apoptosis (Appenzeller-Herzog, C., and Hall, M. N. (2012). Bidirectional crosstalk between endoplasmic reticulum stress and mTOR signaling. Trends Cell Biol 22, 274-282). In healthy cells, astrin mediated suppression of apoptosis may be beneficial as it prevents cells from undergoing apoptosis upon transient stresses or metabolic challenge. In contrast, in cancer cells astrin mediated mTORC1 and apoptosis suppression can become detrimental as it prevents overgrowing cells from undergoing programmed cell death. The understanding of this process opens new avenues to cancer therapy. Notably, astrin is highly expressed in tumour cells (Buechler, 2009; Valk et al., 2010) and spermatocytes, whereas is appears only at low levels in all other non-cancer tissues (GeneNote analysis, www.genecards.org/cgi-bin/carddisp.pl?gene=SPAG5). Hence, astrin inhibition may allow to modulate mTOR network activity specifically in tumour cells, and this may be particularly beneficial to restore the NFL and achieve apoptosis sensitisation when Akt is hyperactive, a condition often found in aggressive cancers (Spears, M., Cunningham, C. A., Taylor, K. J., Mallon, E. A., Thomas, J. S., Kerr, G. R., Jack, W. J., Kunkler, I. H., Cameron, D. A., Chetty, U., et al. (2012). Proximity ligation assays for isoform-specific Akt activation in breast cancer identify activated Akt1 as a driver of progression. J Pathol 227, 481-489). Defective cell cycle progression in astrin deficient cells could limit astrin's suitability as therapeutic target, but astrin deficient mice (Xue, J., Tarnasky, H. A., Rancourt, D. E., and van Der Hoorn, F. A. (2002). Targeted disruption of the testicular SPAG5/deepest protein does not affect spermatogenesis or fertility. Mol Cell Biol 22, 1993-1997), and rats (Yagi, M., Takenaka, M., Suzuki, K., and Suzuki, H. (2007). Reduced mitotic activity and increased apoptosis of fetal sertoli cells in rat hypogonadic (hgn/hgn) testes. J Reprod Dev 53, 581-589) are viable, without displaying major phenotypes. Thus, it is conceivable to target astrin in human disease without affecting vital functions.

---

The invention claimed is:

1. A method for manufacturing a pharmaceutical composition for treating cancer, wherein said method comprises identifying a compound that modulates the expression, the biological activity and/or the interaction of astrin with raptor in a cell, and wherein said identification comprises the steps of
   a) contacting at least one of astrin, a raptor binding fragment of astrin, a cell expressing astrin, and/or a cell expressing a raptor binding fragment thereof with at least one compound that modulates the expression, the biological activity and/or the interaction of astrin with raptor in a cell, and
   b) identifying a modulation of the expression and/or the binding of astrin or said fragment to raptor in the presence of said at least one compound,
   wherein said compound is selected from the group consisting of small molecule drugs, antisense oligonucleotides, siRNA, mRNA, and antibodies and fragments thereof that specifically interfere with the binding of astrin to raptor, and wherein said method further comprises formulating said compound as identified into a pharmaceutical composition.

2. The method according to claim 1, wherein said modulation is selected from a decrease or an increase of said expression and/or of said binding to raptor.

3. The method according to claim 1, wherein said identifying comprises a method selected from rtPCR, immunoprecipitation and measuring the induction or reduction of apoptosis in said cell.

4. The method according to claim 1, wherein said cell is selected from cancer cells; human non-embryonic stem cells; recombinant host cells expressing astrin or the raptor binding fragment thereof; yeast cells; and recombinant bacterial cells.

5. The method according to claim 1, wherein said raptor binding fragment of astrin comprises the N-terminal head domain of the astrin polypeptide.

6. The method according to claim 1, further comprising testing said compound as identified for its activity to sensitise tumour cells to apoptosis.

* * * * *

SEQUENCE LISTING

<160> NUMBER OF SEQ ID NOS: 1

<210> SEQ ID NO 1
<211> LENGTH: 1179
<212> TYPE: PRT
<213> ORGANISM: Homo Sapiens

<400> SEQUENCE: 1

```
Met Trp Arg Val Lys Lys Leu Ser Leu Ser Leu Ser Pro Ser Pro Gln
1               5                   10                  15

Thr Gly Lys Pro Ser Met Arg Thr Pro Leu Arg Glu Leu Thr Leu Gln
            20                  25                  30

Pro Gly Ala Leu Thr Asn Ser Gly Lys Arg Ser Pro Ala Cys Ser Ser
        35                  40                  45

Leu Thr Pro Ser Leu Cys Lys Leu Gly Leu Gln Glu Gly Ser Asn Asn
    50                  55                  60

Ser Ser Pro Val Asp Phe Val Asn Asn Lys Arg Thr Asp Leu Ser Ser
65                  70                  75                  80

Glu His Phe Ser His Ser Ser Lys Trp Leu Glu Thr Cys Gln His Glu
                85                  90                  95

Ser Asp Glu Gln Pro Leu Asp Pro Ile Pro Gln Ile Ser Ser Thr Pro
            100                 105                 110

Lys Thr Ser Glu Glu Ala Val Asp Pro Leu Gly Asn Tyr Met Val Thr
        115                 120                 125

Ile Val Leu Val Pro Ser Pro Leu Gly Gln Gln Gln Asp Met Ile Phe
    130                 135                 140

Glu Ala Arg Leu Asp Thr Met Ala Glu Thr Asn Ser Ile Ser Leu Asn
145                 150                 155                 160

Gly Pro Leu Arg Thr Asp Asp Leu Val Arg Glu Glu Val Ala Pro Cys
                165                 170                 175

Met Gly Asp Arg Phe Ser Glu Val Ala Ala Val Ser Glu Lys Pro Ile
            180                 185                 190

Phe Gln Glu Ser Pro Ser His Leu Leu Glu Glu Ser Pro Pro Asn Pro
        195                 200                 205

Cys Ser Glu Gln Leu His Cys Ser Glu Ser Leu Ser Ser Arg Thr Glu
    210                 215                 220

Ala Val Arg Glu Asp Leu Val Pro Ser Glu Ser Asn Ala Phe Leu Pro
225                 230                 235                 240

Ser Ser Val Leu Trp Leu Ser Pro Ser Thr Ala Leu Ala Asp Phe Arg
                245                 250                 255

Val Asn His Val Asp Pro Glu Glu Glu Ile Val Glu His Gly Ala Met
            260                 265                 270
```

```
Glu Glu Arg Glu Met Arg Phe Pro Thr His Pro Lys Glu Ser Glu Thr
            275                 280                 285
Glu Asp Gln Ala Leu Val Ser Ser Val Glu Asp Ile Leu Ser Thr Cys
        290                 295                 300
Leu Thr Pro Asn Leu Val Glu Met Glu Ser Gln Glu Ala Pro Gly Pro
305                 310                 315                 320
Ala Val Glu Asp Val Gly Arg Ile Leu Gly Ser Asp Thr Glu Ser Trp
                325                 330                 335
Met Ser Pro Leu Ala Trp Leu Glu Lys Gly Val Asn Thr Ser Val Met
            340                 345                 350
Leu Glu Asn Leu Arg Gln Ser Leu Ser Leu Pro Ser Met Leu Arg Asp
        355                 360                 365
Ala Ala Ile Gly Thr Thr Pro Phe Ser Thr Cys Ser Gly Thr Trp Phe
370                 375                 380
Thr Pro Ser Ala Pro Gln Glu Lys Ser Thr Asn Thr Ser Gln Thr Gly
385                 390                 395                 400
Leu Val Gly Thr Lys His Ser Thr Ser Glu Thr Gln Leu Leu Cys
                405                 410                 415
Gly Arg Pro Pro Asp Leu Thr Ala Leu Ser Arg His Asp Leu Glu Asp
            420                 425                 430
Asn Leu Leu Ser Ser Leu Val Ile Leu Glu Val Leu Ser Arg Gln Leu
        435                 440                 445
Arg Asp Trp Lys Ser Gln Leu Ala Val Pro His Pro Glu Thr Gln Asp
        450                 455                 460
Ser Ser Thr Gln Thr Asp Thr Ser His Ser Gly Ile Thr Asn Lys Leu
465                 470                 475                 480
Gln His Leu Lys Glu Ser His Glu Met Gly Gln Ala Leu Gln Gln Ala
                485                 490                 495
Arg Asn Val Met Gln Ser Trp Val Leu Ile Ser Glu Leu Ile Ser Leu
            500                 505                 510
Leu His Leu Ser Leu Leu His Leu Glu Glu Asp Lys Thr Thr Val Ser
        515                 520                 525
Gln Glu Ser Arg Arg Ala Glu Thr Leu Val Cys Cys Cys Phe Asp Leu
        530                 535                 540
Leu Lys Lys Leu Arg Ala Lys Leu Gln Ser Leu Lys Ala Glu Arg Glu
545                 550                 555                 560
Glu Ala Arg His Arg Glu Glu Met Ala Leu Arg Gly Lys Asp Ala Ala
                565                 570                 575
Glu Ile Val Leu Glu Ala Phe Cys Ala His Ala Ser Gln Arg Ile Ser
            580                 585                 590
Gln Leu Glu Gln Asp Leu Ala Ser Met Arg Glu Phe Arg Gly Leu Leu
        595                 600                 605
Lys Asp Ala Gln Thr Gln Leu Val Gly Leu His Ala Lys Gln Glu Glu
        610                 615                 620
Leu Gln Gln Thr Val Ser Leu Thr Ser Leu Gln Asp Trp Arg Ser
625                 630                 635                 640
Met Gln Leu Asp Tyr Thr Thr Trp Thr Ala Leu Leu Ser Arg Ser Arg
                645                 650                 655
Gln Leu Thr Glu Lys Leu Thr Val Lys Ser Gln Gln Ala Leu Gln Glu
            660                 665                 670
Arg Asp Val Ala Ile Glu Glu Lys Gln Glu Val Ser Arg Val Leu Glu
        675                 680                 685
```

-continued

Gln Val Ser Ala Gln Leu Glu Glu Cys Lys Gly Gln Thr Glu Gln Leu
690                 695                 700

Glu Leu Glu Asn Ser Arg Leu Ala Thr Asp Leu Arg Ala Gln Leu Gln
705                 710                 715                 720

Ile Leu Ala Asn Met Asp Ser Gln Leu Lys Glu Leu Gln Ser Gln His
                725                 730                 735

Thr His Cys Ala Gln Asp Leu Ala Met Lys Asp Glu Leu Leu Cys Gln
                740                 745                 750

Thr Gln Ser Asn Glu Glu Ala Gln Trp Gln Lys Glu Met Ala
            755                 760                 765

Leu Lys His Met Gln Ala Glu Leu Gln Gln Gln Ala Val Leu Ala
770                 775                 780

Lys Glu Val Arg Asp Leu Lys Glu Thr Leu Glu Phe Ala Asp Gln Glu
785                 790                 795                 800

Asn Gln Val Ala His Leu Glu Leu Gly Gln Val Glu Cys Gln Leu Lys
                805                 810                 815

Thr Thr Leu Glu Val Leu Arg Glu Arg Ser Leu Gln Cys Glu Asn Leu
            820                 825                 830

Lys Asp Thr Val Glu Asn Leu Thr Ala Lys Leu Ala Ser Thr Ile Ala
                835                 840                 845

Asp Asn Gln Glu Gln Asp Leu Glu Lys Thr Arg Gln Tyr Ser Gln Lys
850                 855                 860

Leu Gly Leu Leu Thr Glu Gln Leu Gln Ser Leu Thr Leu Phe Leu Gln
865                 870                 875                 880

Thr Lys Leu Lys Glu Lys Glu Gln Glu Thr Leu Leu Leu Ser Thr Ala
                885                 890                 895

Cys Pro Pro Thr Gln Glu His Pro Leu Pro Asn Asp Arg Thr Phe Leu
            900                 905                 910

Gly Ser Ile Leu Thr Ala Val Ala Asp Glu Glu Pro Glu Ser Thr Pro
        915                 920                 925

Val Pro Leu Leu Gly Ser Asp Lys Ser Ala Phe Thr Arg Val Ala Ser
    930                 935                 940

Met Val Ser Leu Gln Pro Ala Glu Thr Pro Gly Met Glu Glu Ser Leu
945                 950                 955                 960

Ala Glu Met Ser Ile Met Thr Thr Glu Leu Gln Ser Leu Cys Ser Leu
                965                 970                 975

Leu Gln Glu Ser Lys Glu Glu Ala Ile Thr Leu Gln Arg Lys Ile Cys
            980                 985                 990

Glu Leu Gln Ala Arg Leu Gln Ala Gln Glu Glu Gln His Gln Glu Val
            995                 1000                1005

Gln Lys Ala Lys Ala Asp Ile Glu Lys Leu Asn Gln Ala Leu Cys
    1010                1015                1020

Leu Arg Tyr Lys Asn Glu Lys Glu Leu Gln Glu Val Ile Gln Gln
    1025                1030                1035

Gln Asn Glu Lys Ile Leu Glu Gln Ile Asp Lys Ser Gly Glu Leu
    1040                1045                1050

Ile Ser Leu Arg Glu Glu Val Thr His Leu Thr Arg Ser Leu Arg
    1055                1060                1065

Arg Ala Glu Thr Glu Thr Lys Val Leu Gln Glu Ala Leu Ala Gly
    1070                1075                1080

Gln Leu Asp Ser Asn Cys Gln Pro Met Ala Thr Asn Trp Ile Gln
    1085                1090                1095

Glu Lys Val Trp Leu Ser Gln Glu Val Asp Lys Leu Arg Val Phe

|      |      |      |      |      | 1100 |      |      |      |      | 1105 |      |      |      |      | 1110 |      |      |
|------|------|------|------|------|------|------|------|------|------|------|------|------|------|------|------|------|------|
| Leu  | Glu  | Met  | Lys  | Asn  | Glu  | Lys  | Glu  | Lys  | Leu  | Met  | Ile  | Lys  | Phe  | Gln  |      |      |      |
|      |      |      |      |      | 1115 |      |      |      |      | 1120 |      |      |      |      | 1125 |      |      |
| Ser  | His  | Arg  | Asn  | Ile  | Leu  | Glu  | Glu  | Asn  | Leu  | Arg  | Ser  | Asp  | Lys  | Glu  |      |      |      |
|      |      |      |      |      | 1130 |      |      |      |      | 1135 |      |      |      |      | 1140 |      |      |
| Leu  | Glu  | Lys  | Leu  | Asp  | Asp  | Ile  | Val  | Gln  | His  | Ile  | Tyr  | Lys  | Thr  | Leu  |      |      |      |
|      |      |      |      |      | 1145 |      |      |      |      | 1150 |      |      |      |      | 1155 |      |      |
| Leu  | Ser  | Ile  | Pro  | Glu  | Val  | Val  | Arg  | Gly  | Cys  | Lys  | Glu  | Leu  | Gln  | Gly  |      |      |      |
|      |      |      |      |      | 1160 |      |      |      |      | 1165 |      |      |      |      | 1170 |      |      |
| Leu  | Leu  | Glu  | Phe  | Leu  | Ser  |      |      |      |      |      |      |      |      |      |      |      |      |
|      |      |      |      |      | 1175 |      |      |      |      |      |      |      |      |      |      |      |      |